(12) United States Patent
Dietrich et al.

(10) Patent No.: US 11,685,186 B2
(45) Date of Patent: Jun. 27, 2023

(54) OMNIDIRECTIONAL CHASSIS FOR A GANTRY OF A COMPUTED TOMOGRAPHY DEVICE

(71) Applicant: Siemens Healthcare GmbH, Erlangen (DE)

(72) Inventors: Florian Dietrich, Baiersdorf (DE); Franz Dirauf, Bad Staffelstein (DE); Boban Jovic, Pressarth (DE); Hans-Juergen Mueller, Pretzfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 952 days.

(21) Appl. No.: 16/458,240

(22) Filed: Jul. 1, 2019

(65) Prior Publication Data

US 2020/0016927 A1 Jan. 16, 2020

(30) Foreign Application Priority Data

Jul. 12, 2018 (DE) .......................... 102018211669.5

(51) Int. Cl.
*B60B 19/00* (2006.01)
*A61B 50/13* (2016.01)
(Continued)

(52) U.S. Cl.
CPC .......... *B60B 19/003* (2013.01); *A61B 6/4405* (2013.01); *A61B 50/13* (2016.02);
(Continued)

(58) Field of Classification Search
CPC ..... B60B 19/003; A61B 50/13; A61B 6/4405; A61B 6/032
See application file for complete search history.

(56) References Cited

U.S. PATENT DOCUMENTS 3,876,255 A * 4/1975 Ilon ....................... B60B 19/003
  301/5.1
5,327,474 A * 7/1994 Inoue ..................... A61B 6/032
  378/116
(Continued)

FOREIGN PATENT DOCUMENTS

CN       101072998 A      11/2007
CN       203226834 U      10/2013
(Continued)

OTHER PUBLICATIONS

Korean Office Action and English translation thereof dated Dec. 1, 2020.
(Continued)

*Primary Examiner* — Brian L Swenson
(74) *Attorney, Agent, or Firm* — Harness, Dickey & Pierce, P.L.C.

(57) ABSTRACT

An embodiment relates to an omnidirectional chassis for a gantry of a computed tomography device. The omnidirectional chassis includes a first pair of omnidirectional wheels; and a first wheel suspension for the first pair of omnidirectional wheels. The first wheel suspension includes a connecting unit to connect the first wheel suspension to a rack; a swivel unit connected to the connecting unit via a first swivel bearing and swivel-mounted about a first swivel axis relative to the connecting unit; and a tandem unit, connected to the swivel unit via a second swivel bearing and swivel-mounted about a second swivel axis. In an embodiment, the first pair of omnidirectional wheels is coupled to the tandem unit such that, on a swivel movement of the tandem unit about the second swivel axis, one omnidirectional wheel of the first pair of omnidirectional wheels is relatively raised and another omnidirectional wheel is relatively lowered.

27 Claims, 7 Drawing Sheets

(51) Int. Cl.
*A61B 6/00* (2006.01)
*G05D 1/02* (2020.01)
*A61B 6/03* (2006.01)

(52) U.S. Cl.
CPC .............. *G05D 1/021* (2013.01); *A61B 6/032* (2013.01); *G05D 2201/0206* (2013.01)

(56) References Cited

U.S. PATENT DOCUMENTS

| | | | |
|---|---|---|---|
| 7,188,998 B2* | 3/2007 | Gregerson | A61B 6/4441 378/197 |
| 9,554,953 B2 | 1/2017 | Dirauf et al. | |
| 10,687,770 B2* | 6/2020 | Sullivan | A61B 6/032 |
| 10,792,001 B2* | 10/2020 | Hoernig | A61B 6/4405 |
| 11,395,636 B2* | 7/2022 | Meyer | A61G 7/08 |
| 2003/0235266 A1 | 12/2003 | Gregerson et al. | |
| 2006/0078091 A1 | 4/2006 | Lasiuk et al. | |
| 2013/0200269 A1* | 8/2013 | Abraham | G01T 1/1647 250/395 |
| 2015/0216746 A1* | 8/2015 | Dirauf | B62D 15/00 701/25 |
| 2017/0196748 A1 | 7/2017 | Gaiser | |
| 2017/0215826 A1 | 8/2017 | Johnson et al. | |
| 2017/0215827 A1 | 8/2017 | Johnson et al. | |
| 2017/0325763 A1 | 11/2017 | Hoernig et al. | |
| 2018/0297396 A1 | 10/2018 | Dietrich et al. | |
| 2019/0099141 A1* | 4/2019 | Garlow | A61B 6/547 |
| 2019/0160865 A1 | 5/2019 | Bhat et al. | |

FOREIGN PATENT DOCUMENTS

| | | |
|---|---|---|
| CN | 105882783 A | 8/2016 |
| CN | 106006466 A | 10/2016 |
| CN | 205658063 U | 10/2016 |
| CN | 206085049 U | 4/2017 |
| CN | 108058689 A | 5/2018 |
| DE | 60315642 T2 | 6/2008 |
| DE | 102008023645 A1 | 11/2009 |
| DE | 102014115901 A1 | 5/2016 |
| DE | 102015206909 A1 | 10/2016 |
| DE | 102015107102 A1 | 11/2016 |
| DE | 102016208123 A1 | 9/2017 |
| WO | WO 2016177806 A1 | 11/2016 |
| WO | WO 2018024909 A1 | 2/2018 |

OTHER PUBLICATIONS

Korean Notice of Allowance dated Jun. 10, 2021.
German Office Action for German Application No. 102018211669.5 dated Apr. 4, 2019.

* cited by examiner

OMNIDIRECTIONAL CHASSIS FOR A GANTRY OF A COMPUTED TOMOGRAPHY DEVICE

PRIORITY STATEMENT

The present application hereby claims priority under 35 U.S.C. § 119 to German patent application number DE 102018211669.5 filed Jul. 12, 2018, the entire contents of each of which are hereby incorporated herein by reference.

FIELD

Embodiments of the invention generally relate to an omnidirectional chassis for a gantry of a computed tomography device; an arrangement with a gantry of a computed tomography device and an omnidirectional chassis; and to a method for correcting a movement of a gantry of a computed tomography device.

BACKGROUND

Computed tomography devices are usually mounted stationarily on the ground. The patient table executes a linear movement with which the patient is moved through the scanning plane of the rotating X-ray system in order to perform a helical volume scan, for example.

For certain applications, for example if the X-ray device is used in operating theatres or for radiotherapy, the gantry of the computed tomography device has to be mounted on a mobile platform. Hence, the computed tomography device can be moved toward a patient table or an operating table for the performance of the scan. It is possible that the mobile platform of the computed tomography device executes the linear scanning movement while, for example, the operating table or the patient table on which the patient is mounted for radiotherapy is not moved.

US 2017/0325763 A1 discloses an arrangement with a gantry of a medical imaging apparatus and an omnidirectional chassis for moving the arrangement relative to a support.

U.S. Pat. No. 9,554,953 B2 discloses a medical device including a chassis, wherein the medical device is embodied by way of the chassis to perform a movement in at least two spatial directions on a plane of motion and to execute a rotary movement about an axis of rotation standing perpendicularly on the plane of motion.

SUMMARY

To date, so-called sliding gantries have been mounted on fixed rails, which are embedded in the floor. The inventors have discovered that to date, gantries are typically restricted to a very limited range of travel, for example between two rooms. Also, the inventors have discovered that extensive and costly construction measures are required for the installation.

At least one embodiment of the invention is directed to an improved omnidirectional chassis for a gantry of a computed tomography device.

The claims relate to further advantageous aspects of the invention.

At least one embodiment of the invention relates to an omnidirectional chassis for a gantry of a computed tomography device comprising:

a first pair of omnidirectional wheels; and a first wheel suspension for the first pair of omnidirectional wheels, the first wheel suspension including a connecting unit to connect the first wheel suspension to a rack, a swivel unit, connected to the connecting unit via a first swivel bearing and swivel-mounted about a first swivel axis relative to the connecting unit, and a tandem unit, connected to the swivel unit via a second swivel bearing and swivel-mounted about a second swivel axis, the second swivel axis being substantially parallel to the first swivel axis, relative to the swivel unit, wherein the first pair of omnidirectional wheels is coupled to the tandem unit such that, on a swivel movement of the tandem unit about the second swivel axis, one omnidirectional wheel of the first pair of omnidirectional wheels is relatively raised and another omnidirectional wheel of the first pair of omnidirectional wheels is relatively lowered.

At least one embodiment of the invention further relates an arrangement, comprising:

a gantry of a computed tomography device; and an omnidirectional chassis to move the arrangement relative to a support, wherein the omnidirectional chassis includes four pairs of omnidirectional wheels, wherein the gantry includes a substantially rectangular layout, and wherein each pair of omnidirectional wheels, of the four pairs of omnidirectional wheels, is respectively arranged on each respective corner of four corners of the rectangular layout of the gantry.

At least one embodiment of the invention further relates an arrangement comprising a gantry of a computed tomography device and an omnidirectional chassis for moving the arrangement relative to a support, wherein the omnidirectional chassis is embodied in accordance with one of the disclosed aspects. A support can in particular be the ground, for example a floor of an examination room, or a baseplate.

At least one embodiment of the invention further relates to an arrangement comprising a gantry of a computed tomography device and an omnidirectional chassis for moving the arrangement relative to a support, wherein the omnidirectional chassis comprises four pairs of omnidirectional wheels, wherein the gantry has a substantially rectangular layout, wherein in each case one of the four pairs of omnidirectional wheels is arranged on each respective corner of four corners of the rectangular layout of the gantry.

At least one embodiment of the invention further relates a method for correcting a movement of a gantry of a computed tomography device, the method comprising:

moving the gantry of the computed tomography device via an omnidirectional chassis along a region to be depicted of an examination object, the gantry including an X-ray source and an X-ray detector;

recording projection data from a region to be depicted of the examination object via the X-ray source and the X-ray detector, during the moving of the gantry of the computed tomography device via the omnidirectional chassis;

recording positional information relating to at least one of a position of the gantry of the computed tomography device and an orientation of the gantry of the computed tomography device, during the recording of the projection data;

determining motion correction data based on the positional information recorded during the recording; and correcting movement of the gantry of the computed tomography device by effecting at least one of a change of direction of the movement of the omnidirectional chassis and a change of speed of the movement of the omnidirectional chassis, based upon the motion correction data determined during the recording of the projection data.

In one embodiment, a method for correcting a movement of a gantry of a medical imaging apparatus is disclosed, wherein the method comprises:

moving the gantry of the medical imaging apparatus via an omnidirectional chassis along a region to be depicted of an examination object, wherein the gantry comprises an acquisition unit, recording acquisition data from the region to be depicted of the examination object via the acquisition unit while the gantry of the medical imaging apparatus is moved via the omnidirectional chassis, recording positional information relating to a position of the gantry and/or an orientation of the gantry of the medical imaging apparatus, in particular relative to at least one marking, while the acquisition data is recorded, determination of motion correction data based on the positional information, and correction of the movement of the gantry of the medical imaging apparatus in that a change of direction and/or a change of speed of the movement of the omnidirectional chassis is performed based on the motion correction data, while the acquisition data is recorded.

Without restricting the general concept of the invention, a computed tomography device is cited as an example of a medical imaging apparatus for some of the embodiments.

According to one embodiment of the invention, the medical imaging apparatus comprises an acquisition unit embodied to acquire the acquisition data. In particular, the acquisition unit can comprise a radiation source and a radiation detector.

In the following, the invention is explained with reference to example embodiments and with reference to the attached figures. The depiction in the figures is schematic, greatly simplified and not necessarily true to scale.

Figure 1:
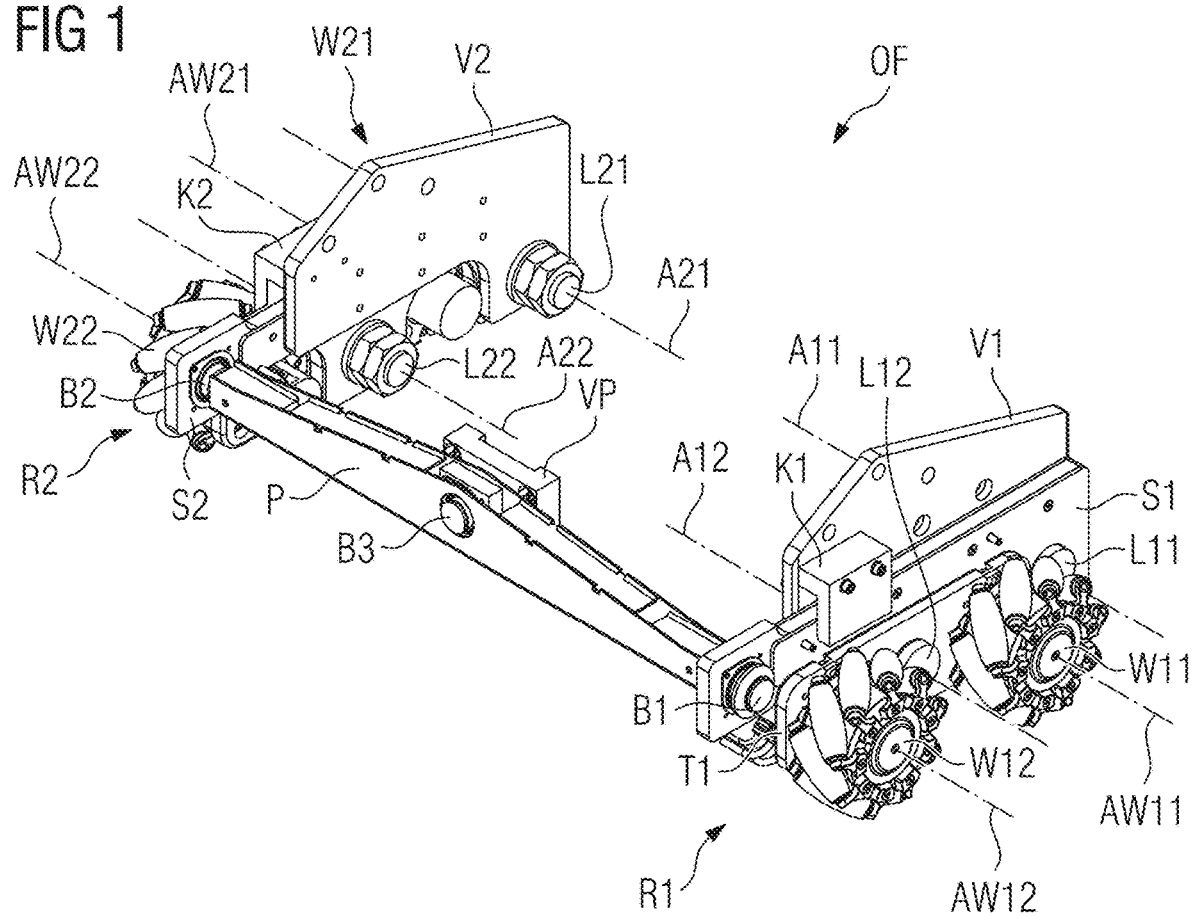
FIG. 1 shows an omnidirectional chassis.

Without restricting general concept of the invention, some of the figures show a medical imaging apparatus in the form of a computed tomography device by way of example.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to an omnidirectional chassis for a gantry of a computed tomography device comprising:
    a first pair of omnidirectional wheels,
    a first wheel suspension for the first pair of omnidirectional wheels,
    wherein the first wheel suspension comprises the following components:
        a connecting unit for connecting the first wheel suspension to a rack, a swivel unit, which is connected to the connecting unit via a first swivel bearing and is swivel-mounted about a first swivel axis relative to the connecting unit, a tandem unit, which is connected to the swivel unit via a second swivel bearing and swivel-mounted about a second swivel axis relative to the swivel unit, which is substantially parallel to the first swivel axis, wherein the first pair of omnidirectional wheels is coupled to the tandem unit such that, on a swivel movement of the tandem unit about the second swivel axis, one omnidirectional wheel of the first pair of omnidirectional wheels is raised and the other omnidirectional wheel of the first pair of omnidirectional wheels is lowered.

At least one embodiment provides that a first omnidirectional wheel of the first pair of omnidirectional wheels is connected to the tandem unit via a first pivot bearing and is pivotably mounted about a first wheel axis relative to the tandem unit, that a second omnidirectional wheel of the first pair of omnidirectional wheels is connected to the tandem unit via a second pivot bearing and is pivotably mounted about a second wheel axis relative to the tandem unit, and that the second swivel axis is arranged in the region of the tandem unit with reference to a horizontal direction between the first wheel axis and the second wheel axis.

At least one embodiment provides that the first swivel axis, the second swivel axis, the first wheel axis and the second wheel axis are substantially parallel to one another.

In particular, the first swivel axis, the second swivel axis, the first wheel axis and the second wheel axis can in each case be horizontal. In particular, at least in one operating state, the first swivel axis, the second swivel axis, the first wheel axis and the second wheel axis the gantry can be arranged substantially parallel to the axis of rotation of the rotor on which the X-ray source and the X-ray detector are arranged for rotation about the axis of rotation.

At least one embodiment provides that the connecting unit, the swivel unit and the tandem unit are in each case embodied as flat, that the first swivel axis is perpendicular to the connecting unit and the swivel unit, and that the second swivel axis is perpendicular to the swivel unit and the tandem unit.

At least one embodiment provides an omnidirectional chassis further comprising:

a second pair of omnidirectional wheels, a second wheel suspension for the second pair of omnidirectional wheels, wherein the second wheel suspension comprises the following components:

a connecting unit for connecting the second wheel suspension to the rack, a swivel unit, which is connected to the connecting unit via a first swivel bearing and is swivel-mounted about a first swivel axis relative to the connecting unit, a tandem unit, which is connected to the swivel unit via a second swivel bearing and is swivel-mounted about a second swivel axis, which is substantially parallel to the first swivel axis relative to the swivel unit, wherein the second pair of omnidirectional wheels is coupled to the tandem unit such that, on a swivel movement of the tandem unit about the second swivel axis, one omnidirectional wheel of the second pair of omnidirectional wheels is raised and the other omnidirectional wheel of the second pair of omnidirectional wheels is lowered.

In particular, in at least one embodiment, the omnidirectional chassis can comprise the first swivel bearing of the first wheel suspension and the second swivel bearing of the first wheel suspension. In particular, the omnidirectional chassis can comprise the first swivel bearing of the second wheel suspension and the second swivel bearing of the of the second wheel suspension. In particular, the first swivel axis of the first wheel suspension and/or the second swivel axis of the first wheel suspension can be horizontal. In particular, the first swivel axis of the second wheel suspension and/or the second swivel axis of the second wheel suspension can be horizontal.

At least one embodiment provides an omnidirectional chassis further comprising a pendulum rod, which is connected to the swivel unit of the first wheel suspension via a first self-aligning bearing and is connected to the swivel unit of the second wheel suspension via a second self-aligning bearing.

At least one embodiment provides that the first swivel axis of the first wheel suspension, the second swivel axis of the first wheel suspension, the first wheel axis of the first wheel suspension, the second wheel axis of the first wheel suspension, the first swivel axis of the second wheel suspension, the second swivel axis of the second wheel suspension, the first wheel axis of the second wheel suspension, the second wheel axis of the second wheel suspension, a center axis of the first self-aligning bearing and a center axis of the second self-aligning bearing are substantially parallel to one another.

A center axis of a self-aligning bearing can in particular be understood to be a rotational axis of symmetry of the self-aligning bearing in a basic state of the self-aligning bearing.

At least one embodiment provides an omnidirectional chassis further comprising:

a connecting element for connecting the pendulum rod to the rack, wherein the pendulum rod is connected to the connecting element via a third self-aligning bearing, wherein the swivel unit of the first wheel suspension and the swivel unit of the second wheel suspension are coupled to the pendulum rod such that, on a pendulum movement of the pendulum rod relative to the connecting element, one of the two swivel units is raised and the other one of the two swivel units is lowered.

This, in particular in the case of unevenness of the support, enables continuous contact between all the omnidirectional wheels and the support and uniform distribution of the load on the omnidirectional wheels of the omnidirectional chassis.

A swivel bearing can in particular be a rolling-contact bearing, for example in the form of ball bearing or a roller bearing. A self-aligning bearing can in particular be a radial spherical plain bearing or an angularly movable pivot bearing, for example in the form of a pendulum ball bearing or a pendulum roller bearing.

A center axis of the third self-aligning bearing can, for example, be substantially perpendicular, in particular perpendicular, to the center axis of the first self-aligning bearing and to the center axis of the second self-aligning bearing.

At least one embodiment provides that the connecting unit of the first wheel suspension is connected to the rack in a positive fitting manner and/or that the connecting unit of the second wheel suspension is connected to the rack in a positive fitting manner and/or wherein the connecting element is connected to the rack in a positive fitting manner.

At least one embodiment provides that at least one omnidirectional wheel of the first pair of omnidirectional wheels and/or at least one omnidirectional wheel of the second pair of omnidirectional wheels comprises a wheel-hub motor, in particular an electric wheel-hub motor. In particular, a pivot bearing can be integrated in the wheel-hub motor, which is embodied for the pivotable bearing of the respective omnidirectional wheel relative to the tandem unit.

At least one embodiment of the invention further relates an arrangement comprising a gantry of a computed tomography device and an omnidirectional chassis for moving the arrangement relative to a support, wherein the omnidirectional chassis is embodied in accordance with one of the disclosed aspects. A support can in particular be the ground, for example a floor of an examination room, or a baseplate.

At least one embodiment provides that the omnidirectional chassis comprises the rack and/or forms a mobile platform. In particular, the gantry can be arranged on the mobile platform. In particular, a gantry of a conventional computed tomography device can be placed on the mobile platform from above, in particular on the rack of the omnidirectional chassis.

At least one embodiment provides that the gantry comprises a support frame, wherein the support frame of the gantry forms the rack of the omnidirectional chassis.

At least one embodiment provides that the omnidirectional chassis comprises four pairs of omnidirectional wheels, that the gantry has a substantially rectangular layout and that in each case one of the four pairs of omnidirectional wheels is arranged on each of the four corners of the rectangular layout of the gantry.

At least one embodiment of the invention further relates to an arrangement comprising a gantry of a computed tomography device and an omnidirectional chassis for moving the arrangement relative to a support, wherein the omnidirectional chassis comprises four pairs of omnidirectional wheels, wherein the gantry has a substantially rectangular layout, wherein in each case one of the four pairs of omnidirectional wheels is arranged on each of the four corners of the rectangular layout of the gantry.

At least one embodiment provides an arrangement further comprising:
a patient support apparatus,
at least one marking, which is arranged in the region of the patient support apparatus, in particular fixed relative to the patient support apparatus,
a measuring system embodied to record positional information relating to a position of the omnidirectional chassis and/or an orientation of the omnidirectional chassis relative to the at least one marking, and
a drive control unit embodied to control a movement of the omnidirectional chassis based on the positional information.

At least one embodiment provides an arrangement further comprising an image reconstruction unit embodied to perform a correction of an image reconstruction based on the positional information.

At least one embodiment of the invention further relates a method for correcting a movement of a gantry of a computed tomography device, wherein the method comprises:
moving the gantry of the computed tomography device via an omnidirectional chassis along a region to be depicted of an examination object, wherein the gantry comprises an X-ray source and an X-ray detector,
recording projection data from the region to be depicted of the examination object via the X-ray source and the X-ray detector while the gantry of the computed tomography device is moved via the omnidirectional chassis,
recording positional information relating to a position of the gantry and/or an orientation of the gantry of the computed tomography device, in particular relative to at least one marking, while the projection data is acquired,
determination of motion correction data based on the positional information, and
correction of the movement of the gantry of the computed tomography device in that a change of direction and/or a change of speed of the movement of the omnidirectional chassis is performed based on the motion correction data while the projection data is recorded.

The examination object can in particular be a patient. The patient can in particular be located on a patient support surface of a patient support apparatus while the projection data is recorded.

At least one embodiment provides that a medical image from the region to be depicted of the examination object is created by way of an image reconstruction based on the projection data, wherein the image reconstruction is corrected based on the positional information. Hence, it is to a large extent possible to prevent artifacts in the medical image caused, for example, by deviations from the ideal movement trajectory, which, despite the correction of the movement of the gantry, occur during the recording of the projection data.

At least one embodiment provides that each omnidirectional wheel of the first pair of omnidirectional wheels is in each case a Mecanum wheel and/or that each omnidirectional wheel of the second pair of omnidirectional wheels is in each case a Mecanum wheel. A suitable choice of lever lengths for the swivel unit and the tandem unit can achieve a uniform distribution of the load on the omnidirectional wheels.

The number of omnidirectional wheels in particular depends on their load-carrying capacity, the weight to be carried and the load capability of the support, in particular of the floor. A preferred configuration consists of eight omnidirectional wheels mounted in each case in pairs in tandem configuration. Four pairs of omnidirectional wheels enable the relatively high weight of the gantry to be distributed better on the support and hence the load on the support to be reduced.

It is also possible, in each case to arrange a pair of omnidirectional wheels on two adjacent corners of the rectangular layout of the gantry and in each case to arrange an individual omnidirectional wheel on the two other corners of the rectangular layout of the gantry. As an alternative to the wheel-hub motor, the at least one omnidirectional wheel can interact with a motor, in particular with an electric motor, that can drive a rotation of the at least one omnidirectional wheel. In particular, the motor and the at least one omnidirectional wheel can be connected via a transmission and/or via a shaft.

According to an example embodiment, with each pair of omnidirectional wheels of the omnidirectional chassis, each of the two omnidirectional wheels comprises a wheel-hub motor. According to a further example embodiment, with each pair of omnidirectional wheels of the omnidirectional chassis, exactly one of the two omnidirectional wheels comprises a wheel-hub motor, wherein the other omnidirectional wheel is in particular embodied without its own drive. For example, the omnidirectional chassis can comprise four pairs of omnidirectional wheels, wherein each of the four pairs of omnidirectional wheels comprises exactly one omnidirectional wheel, which comprises a wheel-hub motor.

At least one embodiment provides that at least one omnidirectional wheel of the first pair of omnidirectional wheels and/or at least one omnidirectional wheel of the second pair of omnidirectional wheels comprises an angular position sensor for recording angular position data of the omnidirectional wheel and/or an angular rate sensor for recording angular rate data of the omnidirectional wheel. The angular position sensor and/or the angular rate sensor can, for example, be integrated in the wheel-hub motor of the at least one omnidirectional wheel or arranged separately from the wheel-hub motor of the at least one omnidirectional wheel.

At least one embodiment provides that at least one omnidirectional wheel of the first pair of omnidirectional wheels and/or at least one omnidirectional wheel of the second pair of omnidirectional wheels comprises a motor regulating unit and/or interacts with a motor regulating unit, wherein the motor regulating unit is embodied to regulate the wheel-hub motor of the at least one omnidirectional wheel based on the angular position data and/or based on the angular rate data.

The motor regulating units of the omnidirectional wheels interact with a drive control unit such that each of the omnidirectional wheels is individually driven by the respective wheel-hub motor in order to execute a desired resultant movement trajectory of the omnidirectional chassis.

The omnidirectional chassis can, for example, comprise an energy storage unit, in particular with accumulators, and/or an energy supply interface for supplying electric energy. One embodiment provides that the energy supply interface of the omnidirectional chassis can be connected to a stationary energy supply unit via a cable. The motors, in particular the wheel-hub motors, the sensors and the motor regulating units can, for example, be operated with electric energy from the energy storage unit and/or from the stationary energy supply unit.

The mobile suspension of the omnidirectional wheels with load equalization and the arrangement in tandem configuration enables it to be ensured that each omnidirectional wheel of the omnidirectional chassis remains in contact with the ground even in the case of unevenness of the ground and is in each case able to accept the share of the overall loads assigned to it. This avoids temporary overloading of individual omnidirectional wheels and excessive localized loading of the floor.

Further solutions are conceivable for establishing contact between omnidirectional wheels and the ground even in the case of unevenness of the ground and a uniform distribution of the load on the omnidirectional wheels. Hereby, in particular an omnidirectional chassis with a plurality of omnidirectional wheels is disclosed, wherein each omnidirectional wheel of the plurality of omnidirectional wheels is suspended on an individual wheel suspension. In particular, the individual wheel suspensions of the omnidirectional wheels of the omnidirectional chassis can interact such that each omnidirectional wheel of the plurality of omnidirectional wheels is kept constant and with uniform loading on the ground.

Hereby, in particular an omnidirectional chassis with a plurality of omnidirectional wheels is disclosed, wherein each omnidirectional wheel of the plurality of omnidirectional wheels is connected to the rack via a spring-shock absorber system. In particular, each omnidirectional wheel of the plurality of omnidirectional wheels can in each case be arranged individually on a spring and/or on a hydraulic cylinder. The characteristic curves of the springs and/or the hydraulic cylinder can in particular be adapted such that each omnidirectional wheel of the plurality of omnidirectional wheels is kept constant and with uniform loading on the ground.

For precise tracking during the scan, the omnidirectional chassis has a measuring system, which can be oriented with respect to spatially fixed markings or features and in particular is continuously able to supply measured values for the drive control unit of the omnidirectional chassis. The measuring system can in particular be embodied as a contact-free measuring system. The measuring system can, for example, comprise optical and/or inductive and/or capacitive sensors. In particular, the measuring system can comprise at least one laser scanner and/or at least one camera.

The measuring system can in particular be embodied to record a pose of the omnidirectional chassis relating to a position and/or an orientation of the omnidirectional chassis relative to at least one spatially fixed marking. Based on the pose of the omnidirectional chassis, the omnidirectional wheels of the omnidirectional chassis can be driven via the drive control unit and/or via the motor regulating units such that the omnidirectional chassis moves along a predetermined movement trajectory and/or that the omnidirectional chassis achieves a predetermined target pose. To this end, it is in particular possible to use closed-loop regulation. This in particular enables collision-free movement and precise positioning of the omnidirectional chassis in the room.

A marking can, for example, be a guide line. In particular, a guide line which is parallel to a longitudinal direction of a patient mounted on a patient support apparatus and/or which is arranged at least partially below the patient support apparatus. In particular, a special sensor system can be provided to ensure the omnidirectional chassis moves precisely in the direction of the guide line and/or in the longitudinal direction of the patient during the scanning process.

During the scanning movement, deviations from the predetermined scanning direction and angular orientation of the computed tomography device can be compensated in that the angular rates of the omnidirectional wheels are in each case adapted individually via the drive control unit and/or via the motor regulating units.

The measuring system can further be embodied, during a scanning movement, to record, in particular continuously, positional information relating to the position and/or the orientation of the gantry relative to a predetermined scanning direction. To this end, the measuring system can, for example, comprise an encoder and/or a laser interferometer. This positional information can, for example, be linked with the projection data recorded at a time at which the omnidirectional chassis is in the corresponding position and/or orientation. Based on the positional information, it is, for example, possible for a correction to be performed with reference to a deviation from the predetermined scanning direction during the image reconstruction.

The omnidirectional chassis makes it possible to transport the gantry of the computed tomography device between different rooms within a hospital and to perform a scanning movement of the gantry of the computed tomography device relative to a patient. The scanning movement can in particular be a rectilinear scanning movement for a helix scan. This in particular makes it possible to dispense with a rail system. Furthermore, it is possible for examinations to be performed via a computed tomography device with a gantry that can be moved via the omnidirectional chassis not only on patient tables with a movable patient support surface but also on fixed patient tables, such as, for example, on operating tables or patient tables in a radiotherapy apparatus.

The omnidirectional chassis can in particular be embodied for autonomous movement. The omnidirectional chassis can in particular comprise a user interface, wherein a user is able to control a movement of the omnidirectional chassis via the user interface. The user interface can, for example, comprise a software application. In particular, a graphical user interface of the software application can be displayed on a touch screen, for example a touch screen of a tablet computer.

The user interface can be used to record a user input of the user. The user input can be used to control a movement of the omnidirectional chassis. According to one embodiment, the touch screen can record a force with which user presses the touch screen (force touch) and the movement of the omnidirectional chassis can be controlled based on the force.

Hereby, in particular an omnidirectional chassis for a gantry of a medical imaging apparatus is disclosed comprising:
 a first pair of omnidirectional wheels,
 a first wheel suspension for the first pair of omnidirectional wheels,
 wherein the first wheel suspension comprises the following components:
 a connecting unit for connecting the first wheel suspension to a rack,
 a swivel unit, which is connected to the connecting unit via a first swivel bearing and is swivel-mounted about a first swivel axis relative to the connecting unit,
 a tandem unit, which is connected to the swivel unit via a second swivel bearing and is swivel-mounted about a second swivel axis, which is substantially parallel to the first swivel axis, relative to the swivel unit,
 wherein the first pair of omnidirectional wheels is coupled to the tandem unit such that, on a swivel movement of the tandem unit about the second swivel axis, one omnidirectional wheel of the first pair of omnidirectional wheels is raised and the other omnidirectional wheel of the first pair of omnidirectional wheels is lowered.

The omnidirectional chassis for the gantry of the medical imaging apparatus can in particular be embodied in accordance with one of the aspects disclosed in connection with a computed tomography device.

Hereby, in particular an arrangement is disclosed comprising a gantry of a medical imaging apparatus and an omnidirectional chassis for moving the arrangement relative to a support, wherein the omnidirectional chassis is embodied in accordance with one of the disclosed aspects. This arrangement can in particular be embodied in accordance with one of the aspects of an arrangement disclosed in connection with a computed tomography device.

Hereby, in particular an arrangement is disclosed comprising a gantry of a medical imaging apparatus and an omnidirectional chassis for moving the arrangement relative to a support, wherein the omnidirectional chassis comprises four pairs of omnidirectional wheels, wherein the gantry has a substantially rectangular layout, wherein in each case one of the four pairs of omnidirectional wheels is arranged on each of the four corners of the rectangular layout of the gantry.

In one embodiment, a method for correcting a movement of a gantry of a medical imaging apparatus is disclosed, wherein the method comprises:
 moving the gantry of the medical imaging apparatus via an omnidirectional chassis along a region to be depicted of an examination object, wherein the gantry comprises an acquisition unit,
 recording acquisition data from the region to be depicted of the examination object via the acquisition unit while the gantry of the medical imaging apparatus is moved via the omnidirectional chassis,
 recording positional information relating to a position of the gantry and/or an orientation of the gantry of the medical imaging apparatus, in particular relative to at least one marking, while the acquisition data is recorded,
 determination of motion correction data based on the positional information, and
 correction of the movement of the gantry of the medical imaging apparatus in that a change of direction and/or a change of speed of the movement of the omnidirectional chassis is performed based on the motion correction data, while the acquisition data is recorded.

An embodiment of the method for correcting the movement of the gantry of the medical imaging apparatus can in particular be embodied in accordance with one of the aspects disclosed in connection with a computed tomography device.

The medical imaging apparatus can, for example, be selected from the imaging modality group consisting of an X-ray device, a C-arm X-ray device, a computed tomography device (CT device), a molecular imaging device (MI device), a single photon emission computed tomography device (SPECT device), a positron emission tomography device (PET device), a magnetic resonance tomography device (MR device) and combinations thereof, in particular a PET-CT device and a PET-MR device. The medical imaging apparatus can further comprise a combination of an imaging modality, which is, for example, selected from the imaging modality group, and a radiation modality. Herein, the radiation modality can comprise, for example, a radiation unit for therapeutic radiation.

Without restricting the general concept of the invention, a computed tomography device is cited as an example of a medical imaging apparatus for some of the embodiments.

According to one embodiment of the invention, the medical imaging apparatus comprises an acquisition unit embodied to acquire the acquisition data. In particular, the acquisition unit can comprise a radiation source and a radiation detector.

One embodiment of the invention provides that the radiation source is embodied for the emission and/or excitation of radiation, in particular electromagnetic radiation, and/or that the radiation detector is embodied to detect the radiation, in particular the electromagnetic radiation. The radiation can, for example, travel from the radiation source to a region to be depicted and/or, following interaction with the region to be depicted, to the radiation detector.

During interaction with the region to be depicted, the radiation is modified and hence becomes a carrier of information relating to the region to be depicted. During interaction of the radiation with the detector, this information is recorded in the form of acquisition data.

In particular, in the case of a computed tomography device and a C-arm X-ray device, the acquisition data can be projection data, the acquisition unit can be a projection data-acquisition unit, the radiation source can be an X-ray source and the radiation detector can be an X-ray detector. The X-ray detector can in particular be a quantum-counting and/or energy-resolving X-ray detector.

In particular, in the case of a magnetic resonance imaging device, the acquisition data can be a magnetic resonance dataset, the acquisition unit can be a magnetic resonance data acquisition unit, the radiation source can be a first radio frequency antenna unit and the radiation detector can be the first radio frequency antenna unit and/or a second radio frequency antenna unit.

The gantry of a medical imaging apparatus typically comprises a supporting structure on which in particular components of the acquisition unit, in particular the radiation source and/or the radiation detector, are arranged. The supporting structure of the gantry is typically sufficiently rigid and strong to ensure that the components of the acquisition unit can be arranged in a geometry sufficiently defined for the imaging both relative to one another and relative to a region to be depicted.

In the case of a computed tomography device, the gantry typically comprises a support frame and a rotor pivotably mounted relative to the support frame, wherein the radiation source and the radiation detector are arranged on the rotor. The gantry can optionally comprise a tilt frame mounted tiltably relative to the support frame, wherein the rotor is arranged on the tilt frame.

In the case of a C-arm X-ray device, the gantry typically comprises a support frame and a C-arm swivel-mounted relative to the support frame, wherein the radiation source and the radiation detector are arranged on the C-arm.

In the case of a magnetic resonance imaging device, the gantry typically comprises a support frame on which the main magnet and a first radio frequency antenna unit are arranged, wherein the first radio frequency antenna unit is embodied in the form of a body coil—which is a term known to the person skilled in the art.

In the context of the invention, features, which are described with reference to different embodiments of the invention and/or different claim categories (method, use, apparatus, system, arrangement etc.) can be combined to form further embodiments of the invention. For example, a claim relating to an apparatus can also be developed with features described or claimed in conjunction with a method and vice versa. Herein, functional features of a method can be implemented by correspondingly embodied material components. In addition to the embodiments of the invention expressly described in this application, numerous further embodiments of the invention are conceivable at which the person skilled in the art can arrive without departing from the scope of the invention in so far as it is defined by the claims.

The use of the indefinite article "a" or "an" does not preclude the possibility of the features in question also being present on a multiple basis. The use of the term "comprise" does not preclude the possibility of the terms being linked by way of term "comprise" being identical. For example, the computed tomography device comprises the computed tomography device. The use of the term "unit" does not preclude the possibility of the subject matter to which the term "unit" relates comprising a plurality of components that are spatially separated from one another.

In the following, the invention is explained with reference to example embodiments and with reference to the attached figures. The depiction in the figures is schematic, greatly simplified and not necessarily true to scale.

FIG. 1 shows an omnidirectional chassis OF for a gantry 20 of a computed tomography device 1 comprising a first pair of omnidirectional wheels W11, W12, in the form of Mecanum wheels, a first wheel suspension R1 for the first pair of omnidirectional wheels W11, W12, a second pair of omnidirectional wheels W21, W22 in the form of Mecanum wheels and a second wheel suspension R2 for the second pair of omnidirectional wheels W21, W22.

The first wheel suspension R1 comprises the following components:
a connecting unit V1 for connecting the first wheel suspension R1 to a rack G,
a swivel unit S1, which is connected to the connecting unit V1 via a first swivel bearing L11 and is swivel-mounted about a first swivel axis A11 relative to the connecting unit V1, and
a tandem unit T1, which is connected to the swivel unit S1 via a second swivel bearing L12 and is swivel-mounted about a second swivel axis A12, which is substantially parallel to the first swivel axis A11 relative to the swivel unit S1.

The second wheel suspension R2 comprises the following components:
a connecting unit V2 for connecting the second wheel suspension R2 to the rack G,
a swivel unit S2, which is connected to the connecting unit V2 via a first swivel bearing L21 and is swivel-mounted about a first swivel axis A21 relative to the connecting unit V2,
a tandem unit T2, which is connected to the swivel unit S2 via a second swivel bearing L22 and is swivel-mounted about a second swivel axis A22, which is substantially parallel to the first swivel axis A21, relative to the swivel unit S2.

The first swivel axis A11 of the first wheel suspension R1, the second swivel axis A12 of the first wheel suspension R1, the first wheel axis of the first wheel suspension R1 and the second wheel axis of the first wheel suspension R1, the first swivel axis A21 of the second wheel suspension R2, the second swivel axis A22 of the second wheel suspension R2, the first wheel axis of the second wheel suspension R2, the second wheel axis of the second wheel suspension R2, a center axis of the first self-aligning bearing B1 and a center axis of the second self-aligning bearing B2 are parallel to one another and horizontal.

The connecting unit V1, the swivel unit S1 and the tandem unit T1 are in each case embodied as flat. The first swivel axis A11 is perpendicular to the connecting unit V1 and the swivel unit S1. The second swivel axis A12 is perpendicular to the swivel unit S1 and the tandem unit T1.

The omnidirectional chassis OF comprises a pendulum rod P, which is connected to the swivel unit S1 of the first wheel suspension R1 via the first self-aligning bearing B1 and is connected to the swivel unit S2 of the second wheel suspension R2 via the second self-aligning bearing B2.

The omnidirectional chassis OF comprises a connecting element VP for connecting the pendulum rod P to the rack G. The pendulum rod P is connected to the connecting element VP via the third self-aligning bearing B3. The swivel unit S1 of the first wheel suspension R1 and the swivel unit S2 of the second wheel suspension R2 are coupled to the pendulum rod P such that, on a pendulum movement of the pendulum rod relative to the connecting element VP, one of the two swivel units is raised and the other one of the two swivel units is lowered.

Figure 2:
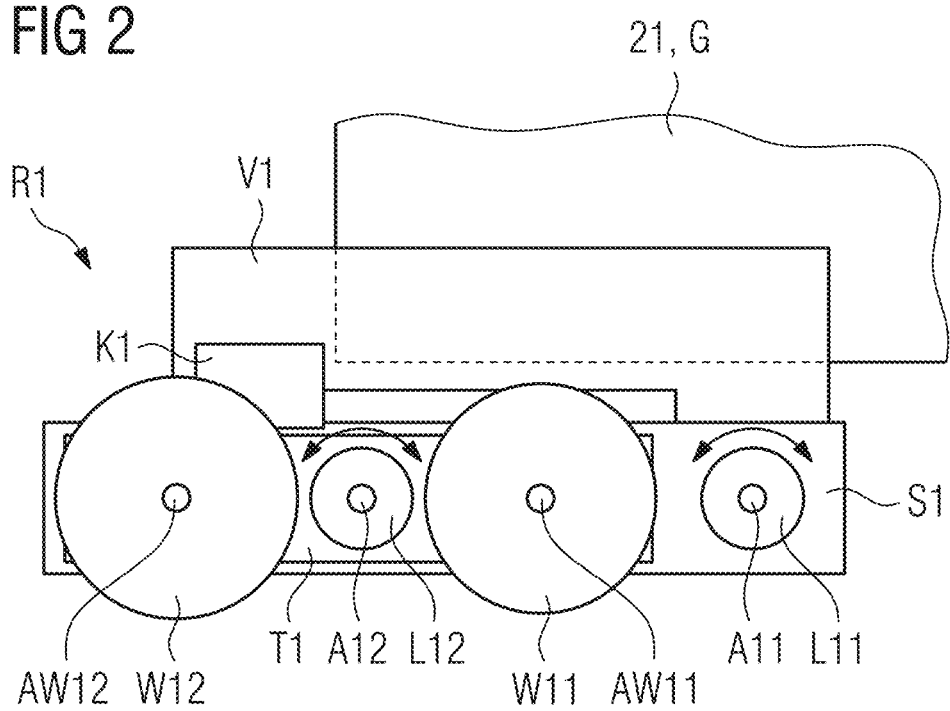
FIG. 2 shows a wheel suspension of the omnidirectional chassis in a first operating state.

FIG. 2 shows the wheel suspension R1 of the omnidirectional chassis OF in a first operating state in which the omnidirectional chassis OF stands on an even region of the support 8.

Figure 3:
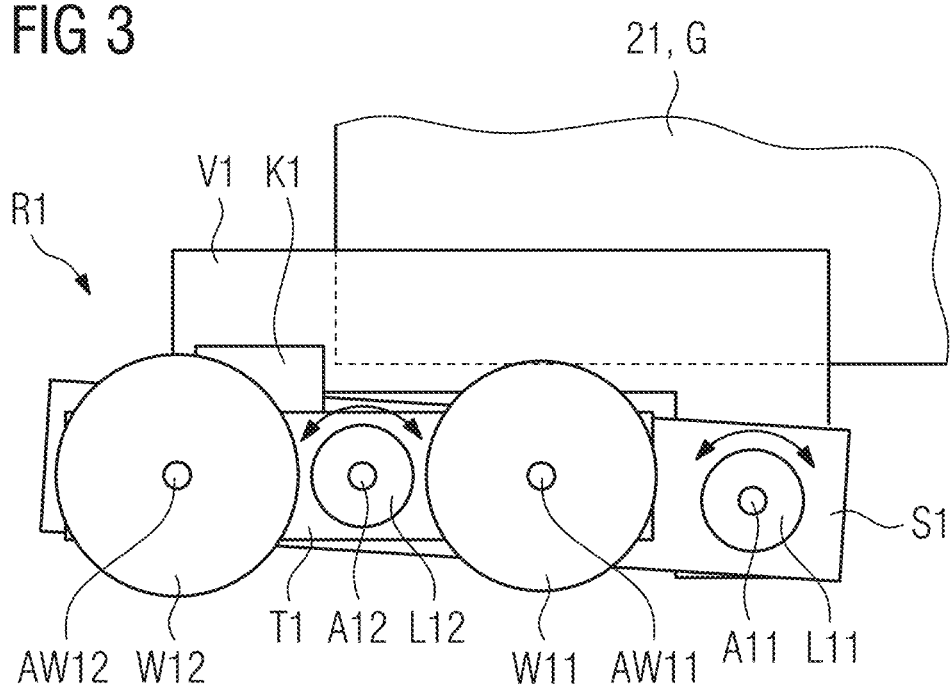
FIG. 3 shows a wheel suspension of the omnidirectional chassis in a second operating state.

FIG. 3 shows the wheel suspension R1 of the omnidirectional chassis OF in a second operating state, in which the omnidirectional chassis OF compensates an unevenness of the support 8. The first pair of omnidirectional wheels W11, W12 is coupled to the tandem unit T1 such that, on a swivel movement of the tandem unit T1 about the second swivel axis A12, one omnidirectional wheel of the first pair of omnidirectional wheels W11, W12 is raised and the other omnidirectional wheel of the first pair of omnidirectional wheels W11, W12 is lowered.

The second pair of omnidirectional wheels W21, W22 is coupled to the tandem unit T2 such that, on a swivel movement of the tandem unit T2 about the second swivel axis A22, one omnidirectional wheel of the second pair of omnidirectional wheels W21, W22 is raised and the other omnidirectional wheel of the second pair of omnidirectional wheels W21, W22 is lowered. The second swivel axis A12 is arranged in the region of the tandem unit T1 with reference to a horizontal direction between the first wheel axis about which the first omnidirectional wheel W11 is pivotably mounted, and the second wheel axis about which the second omnidirectional wheel W12 is pivotably mounted.

The first wheel suspension R1 comprises a first blocking unit K1, which is embodied to limit the upward swivel movement of the swivel unit S1 of the first wheel suspension R1. The second wheel suspension R2 comprises a first blocking unit K2, which is embodied to limit the upward swivel movement of the swivel unit S2 of the second wheel suspension R2.

Figure 4:
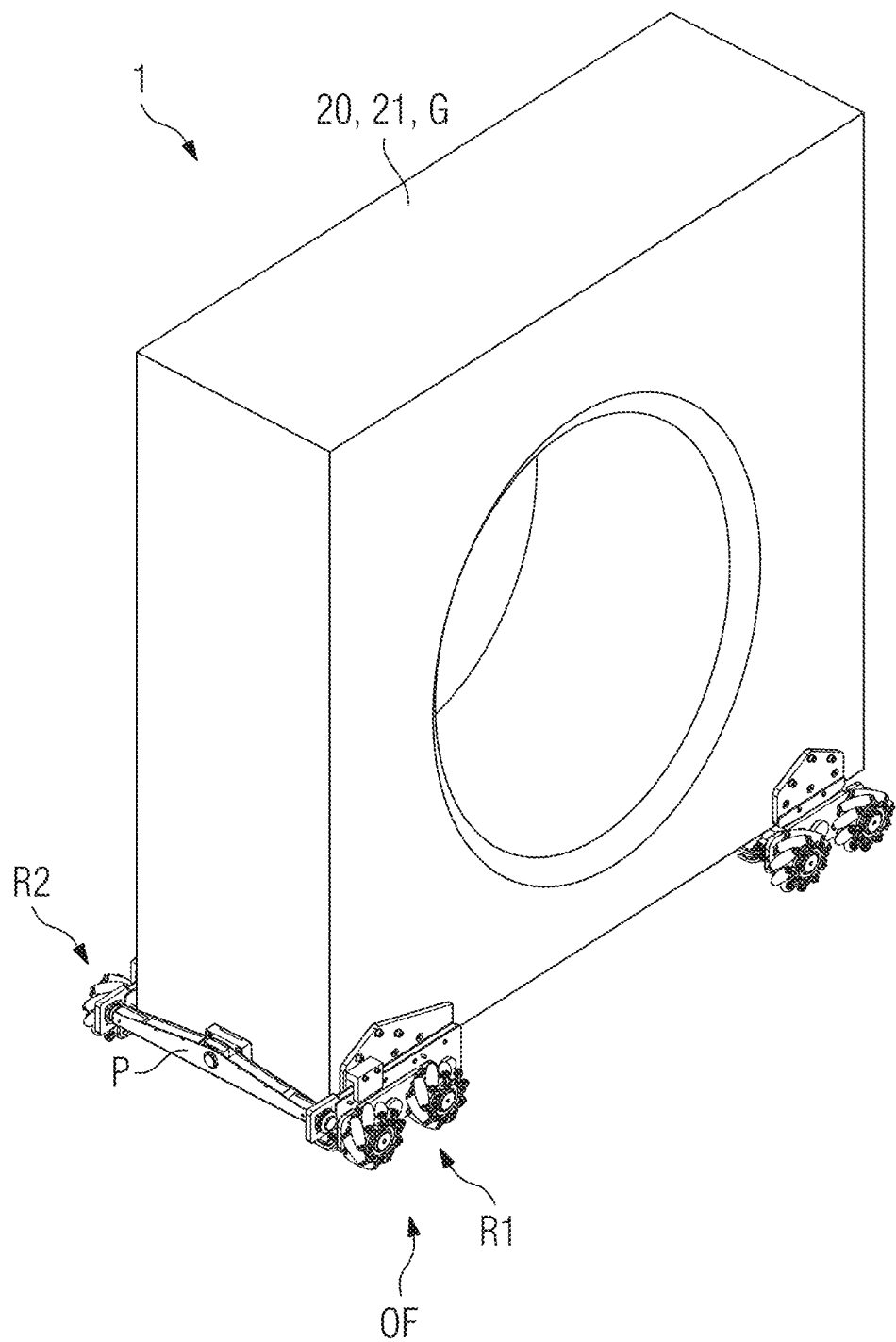
FIG. 4 shows an arrangement with a gantry of a computed tomography device and an omnidirectional chassis.

FIG. 4 shows an arrangement 1 with a gantry 20 of a computed tomography device 2 and the omnidirectional chassis OF for moving the arrangement 1. In the example embodiment shown in FIG. 4, the omnidirectional chassis OF comprises four pairs of Mecanum wheels. The gantry 20 has a substantially rectangular layout, wherein in each case one of the four pairs of Mecanum wheels is arranged on each of the four corners of the rectangular layout of the gantry 20. The gantry 20 comprises a support frame 21. In the example embodiment shown in FIG. 4, the support frame 21 of the gantry 20 forms the rack G of the omnidirectional chassis OF. Herein, four wheel suspensions are in each case connected directly to the support frame 21 via the respective connecting units.

Each of the eight Mecanum wheels in each case comprises an electric wheel-hub motor. However, it is also possible that, in each pair of Mecanum wheels, in each case only one Mecanum wheel comprises an electric wheel-hub motor. Then, four of the total of eight Mecanum wheels would in each case comprise an electric wheel-hub motor. The other four of the total of eight Mecanum wheels would not have a drive and the movement of the omnidirectional chassis would take passively.

Figure 5:
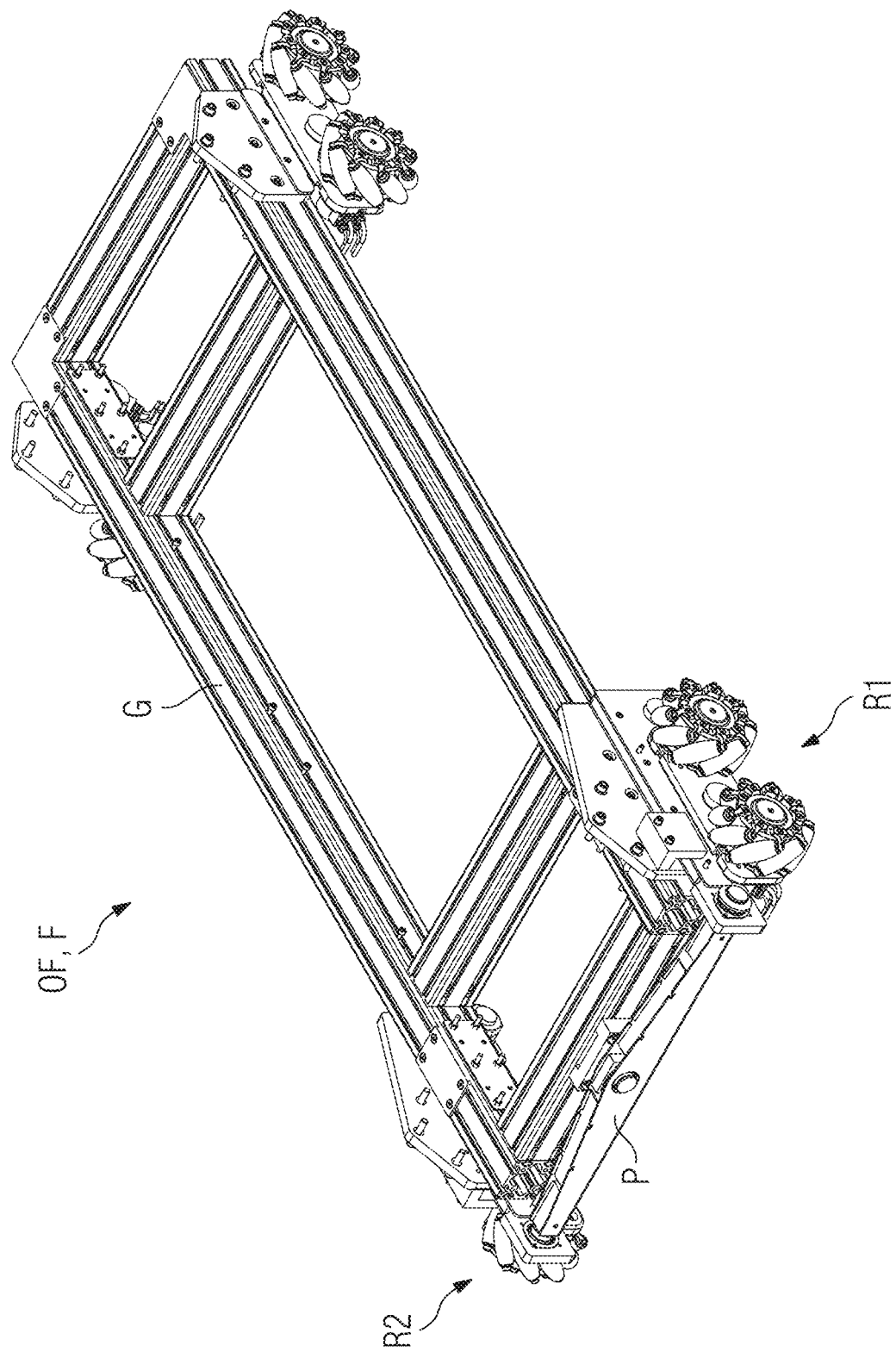
FIG. 5 shows an omnidirectional chassis that forms a mobile platform.

FIG. 5 shows an omnidirectional chassis OF that forms a mobile platform on which the gantry 20 can be arranged and secured. It is, for example, possible for the energy storage unit in the form of accumulators and/or cabling for the Mecanum wheels to be arranged in the mobile platform. The connecting units of the four wheel suspensions are in each case embodied to provide a positive connection with the support frame 21 of the gantry 20.

Figure 6:
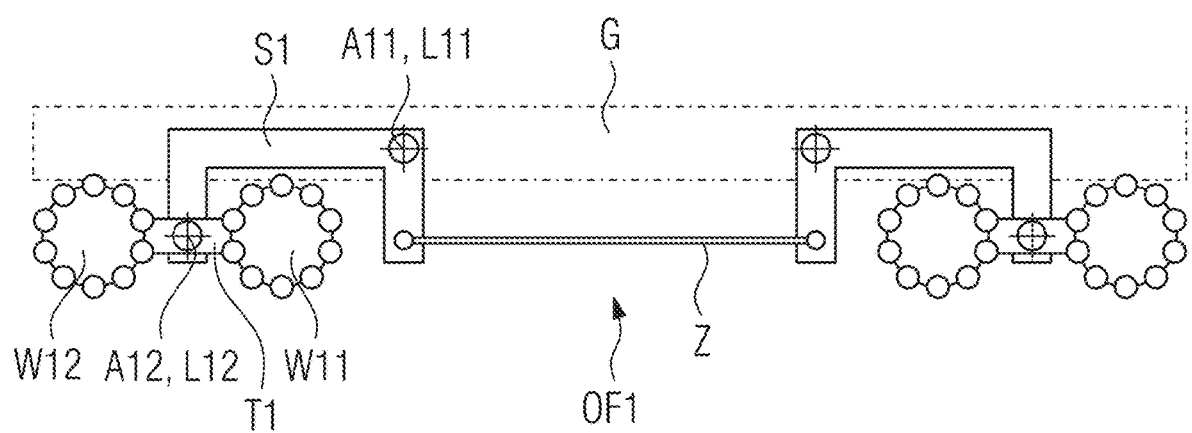
FIG. 6 shows an omnidirectional chassis with a tension rod for load equalization between the omnidirectional wheels.

FIG. 6 shows an omnidirectional chassis OF1 with a tension rod Z for load equalization between the omnidirectional wheels. The omnidirectional wheels of the omnidirectional chassis OF1 are arranged on mobile rockers connected via the tension rod Z. This can also enable continuous contact between the omnidirectional wheels and the ground in the event of unevenness of the ground.

Figure 7:
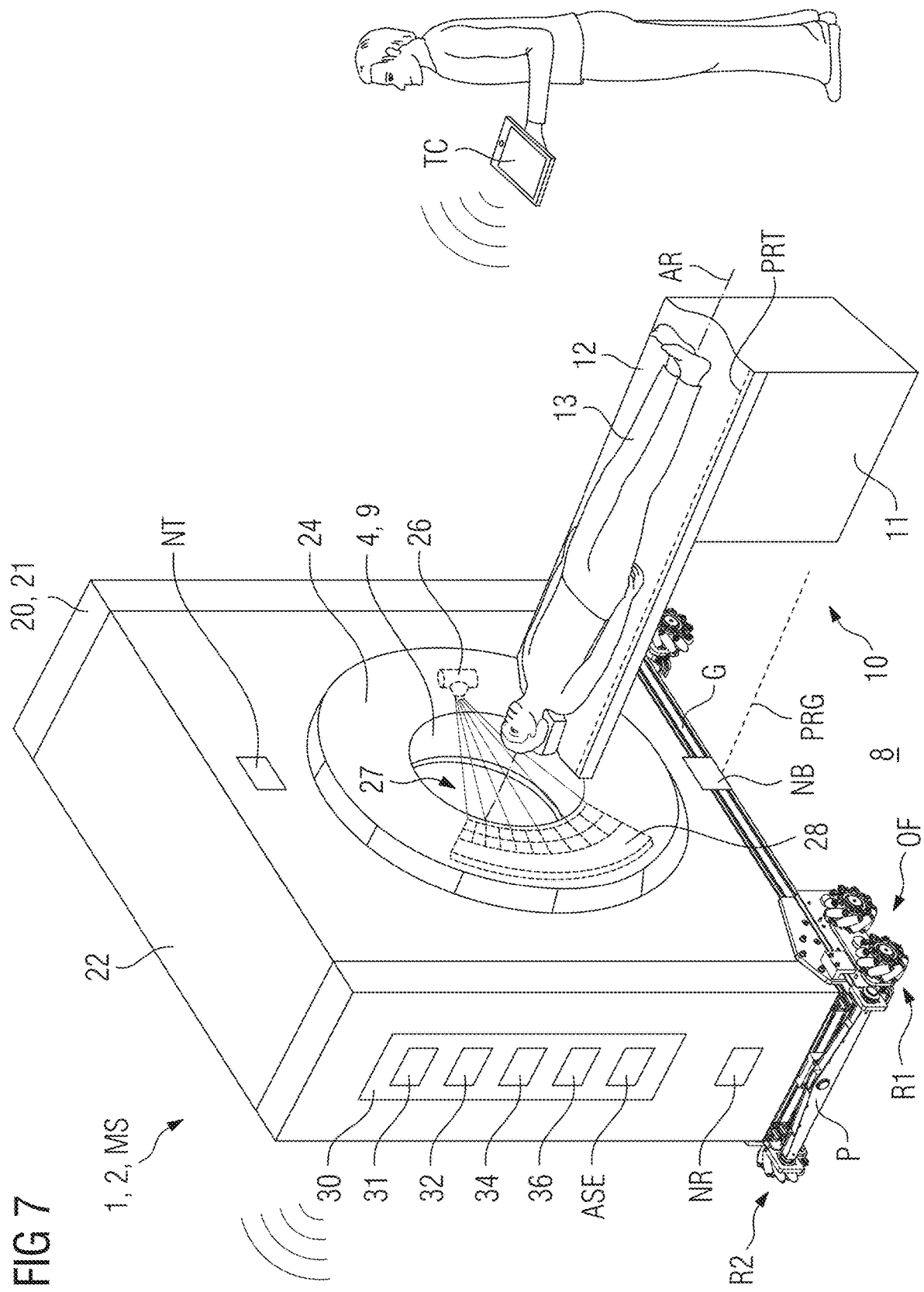
FIG. 7 shows an arrangement with a computed tomography device comprising a gantry arranged on a mobile platform.

FIG. 7 shows an arrangement 1 with a computed tomography device 2 comprising a gantry 20 arranged on a mobile platform according to the example embodiment shown in FIG. 5.

The computed tomography device 2 comprises the gantry 20, the tunnel-shaped opening 9, the patient support apparatus 10 and the control apparatus 30. The gantry 20 comprises the stationary support frame 21, the tilt frame 22 and the rotor 24. The tilt frame 22 is arranged tiltably about a tilting axis relative to the stationary support frame 21 on the stationary support frame 21 via a tilting support apparatus. The rotor 24 is arranged pivotably about the axis of rotation AR relative to the tilt frame 22 on the tilt frame 22 via a pivoting support apparatus. The tilting axis is perpendicular to the axis of rotation AR and horizontal.

The patient 13 can be introduced in the tunnel-shaped opening 9. The acquisition region 4 is located in the tunnel-shaped opening 9. A region of the patient 13 to be depicted can be positioned in the acquisition region 4 such that the radiation 27 can travel from the radiation source 26 to the region to be depicted and, after interaction with the region to be depicted, travel to the radiation detector 28. The patient support apparatus 10 comprises the support base 11 and the support surface 12 for supporting the patient 13. The gantry 20 can be positioned relative to the support surface 12 via the omnidirectional chassis 20 such that the support surface 12 extends into the tunnel-shaped opening 9.

Transportation journeys between the rooms of the hospital and within a room can in particular be carried out such that the omnidirectional chassis OF moves perpendicularly to the wheel axes of the Mecanum wheels. During the acquisition of projection data, the omnidirectional chassis OF can, for example, move parallel to the wheel axes of the Mecanum wheels.

In the operating state of the gantry shown in FIG. 7, the axis of rotation AR about which the X-ray source 26 and the X-ray detector 28 rotate is horizontal and parallel to the wheel axes of the Mecanum wheels. The arrangement 1 comprises a patient support apparatus 10. At least one marking in the form of the guide line PRG is arranged in the region of the patient support apparatus 10. The guide line PRG is plotted on the ground below the patient support plate 12 and extends in the longitudinal direction of the patient 13, who is mounted on the patient support plate.

The guide line PRG can, for example, have a suitable structure so that a change in position along the guide line PRG can be measured with the aid of the structure.

The arrangement 1 further comprises a measuring system MS and the drive control unit ASE. The measuring system MS is embodied to record positional information relating to a position of the omnidirectional chassis OF and/or an orientation of the omnidirectional chassis OF relative to the at least one marking. The measuring system MS in particular comprises the sensors NB, NT and NR. The drive control unit ASE is embodied to control a movement of the omnidirectional chassis OF based on the positional information.

The arrangement 2 further comprises an image reconstruction unit 34, which is embodied to perform a correction of an image reconstruction based on the positional information. A further marking in the form of the linear structure PRT is arranged on the patient support plate 12. Positional information relating to a position of the omnidirectional chassis OF relative to the linear structure PRT, can, for example, be recorded by the measuring system MS via an optical sensor and/or via the projection data-acquisition unit of the computed tomography device 2. This positional information can be used to control a movement of the omnidirectional chassis and/or for the correction of an image reconstruction.

A data transmission interface 31 is integrated in the gantry 20 to enable data to be transmitted from the tablet computer TC and/or to the tablet computer TC, in particular via a wireless network. A touch screen of the tablet computer TC can, for example, display a graphical user interface for controlling the omnidirectional chassis OF and/or for performing an examination via the computed tomography device 2. The tablet computer TC is embodied for the inputting of control information, for example in the form of image reconstruction parameters and/or examination parameters and/or movement trajectories, and for the outputting of control information, for example in the form of images and/or acoustic signals.

The computed tomography device 2 is embodied for the acquisition of acquisition data based on electromagnetic radiation 27. The computed tomography device 2 comprises an acquisition unit. The acquisition unit is a projection data-acquisition unit with the radiation source 26, for example an X-ray source, and the detector 28, for example an X-ray detector, in particular an energy-resolving X-ray detector. The radiation source 26 is arranged on the rotor 24 and embodied for the emission of radiation 27, for example X-rays with radiation quanta 27. The detector 28 is arranged on the rotor 24 and embodied to detect the radiation quanta 27. The radiation quanta 27 can travel from the radiation source 26 to the region of the patient 13 to be depicted and, following interaction with the region to be depicted, arrive at the detector 28. This enables the acquisition unit to record acquisition data of the region to be depicted in the form of projection data.

The control apparatus 30 is embodied to receive the acquisition data acquired by the acquisition unit. The control apparatus 30 is embodied to control the computed tomography device 2. The control apparatus 30 is in particular embodied to determine the motion correction data, based on the positional information.

The control apparatus 30 comprises the data transmission interface 31, the computer-readable medium 32, the processor system 36 and the drive control unit ASE. The control apparatus 30, in particular the drive control unit ASE, is formed by a data processing system comprising a computer. The drive control unit ASE is in particular embodied to effect a change of direction and/or a change of speed of the movement of the omnidirectional chassis OF based on the motion correction data.

The control apparatus 30 further comprises the image reconstruction facility 34. The image reconstruction facility 34 can be used to reconstruct a medical image data set based on the acquisition data. The image reconstruction facility 34 is in particular embodied to correct the image reconstruction based on the positional information.

Figure 8:
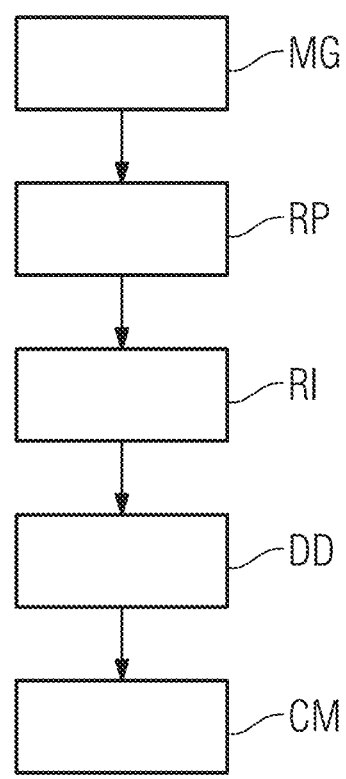
FIG. 8 shows a flowchart of a method for correcting a movement of a gantry of a computed tomography device.

FIG. 8 shows a flowchart of a method for correcting a movement of the gantry 20 of the computed tomography device 2, wherein the method comprises the following steps:

moving MG the gantry MG of the computed tomography device 2 via an omnidirectional chassis OF along a region to be depicted of an examination object 13, wherein the gantry 20 comprises an X-ray source 26 and an X-ray detector 28, recording RP of projection data from the region of the examination object 13 to be depicted by way of the X-ray source 26 and the X-ray detector 28 while the gantry 20 of the computed tomography device 2 is moved via the omnidirectional chassis OF, recording RI of positional information relating to a position of the gantry 20 and/or an orientation of the gantry 20 while the projection data is recorded, determination DD of motion correction data based on the positional information, correction CM of the movement of the gantry 20 of the computed tomography device 2 in that a change of direction and/or a change of speed of the movement of the omnidirectional chassis OF is performed based on the motion correction data while the projection data is recorded.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An omnidirectional chassis for a gantry of a computed tomography device, comprising:
 a first pair of omnidirectional wheels; and
 a first wheel suspension for the first pair of omnidirectional wheels, the first wheel suspension including
   a first connecting unit to connect the first wheel suspension to a rack,
   a first swivel unit connected to the first connecting unit via a first swivel bearing, the first swivel unit being swivel-mounted about a first swivel axis, and
   a first tandem unit connected to the first swivel unit via a second swivel bearing, the first tandem unit being swivel-mounted about a second swivel axis, and the second swivel axis being substantially parallel to the first swivel axis,
 wherein the first pair of omnidirectional wheels is coupled to the first tandem unit such that one omnidirectional wheel among the first pair of omnidirectional wheels is raised in response to a first swivel movement of the first tandem unit about the second swivel axis, and another omnidirectional wheel among the first pair of omnidirectional wheels is lowered in response to the first swivel movement.

2. The omnidirectional chassis of claim 1, wherein a first omnidirectional wheel among the first pair of omnidirectional wheels is connected to the first tandem unit via a first rotary bearing, the first omnidirectional wheel being rotatably mounted about a first wheel axis;

a second omnidirectional wheel among the first pair of omnidirectional wheels is connected to the first tandem unit via a second rotary bearing, the second omnidirectional wheel being rotatably mounted about a second wheel axis; and the second swivel axis is arranged in a region of the first tandem unit between the first wheel axis and the second wheel axis.

3. The omnidirectional chassis of claim 2, wherein the first swivel axis, the second swivel axis, the first wheel axis and the second wheel axis are substantially parallel to one another.

4. The omnidirectional chassis of claim 2, wherein the first connecting unit, the first swivel unit and the first tandem unit each have a flat surface;

the first swivel axis is perpendicular to the flat surface of the first connecting unit and the flat surface of the first swivel unit; and the second swivel axis is perpendicular to the flat surface of the first swivel unit and the flat surface of the first tandem unit.

5. The omnidirectional chassis of claim 2, further comprising:

a second pair of omnidirectional wheels; and a second wheel suspension for the second pair of omnidirectional wheels, the second wheel suspension including a second connecting unit to connect the second wheel suspension to the rack, a second swivel unit, connected to the second connecting unit via a third swivel bearing, the second swivel unit being swivel-mounted about a third swivel axis, and a second tandem unit connected to the second swivel unit via a fourth swivel bearing, the second tandem unit being swivel-mounted about a fourth swivel axis, and the fourth swivel axis being substantially parallel to the third swivel axis, wherein the second pair of omnidirectional wheels is coupled to the second tandem unit such that one omnidirectional wheel among the second pair of omnidirectional wheels is raised in response to a second swivel movement of the second tandem unit, and another omnidirectional wheel among the second pair of omnidirectional wheels is lowered in response to the second swivel movement.

6. The omnidirectional chassis of claim 5, further comprising:

a pendulum rod; connected to the first swivel unit via a first self-aligning bearing, and the second swivel unit via a second self-aligning bearing.

7. The omnidirectional chassis of claim 6, further comprising:

a connecting element to connect the pendulum rod to the rack, the pendulum rod being connected to the connecting element via a third self-aligning bearing, wherein the first swivel unit and the second swivel unit are coupled to the pendulum rod such that one of the first swivel unit or the second swivel unit is raised in response to a pendulum movement of the pendulum rod relative to the connecting element, and another one of the first swivel unit or the second swivel unit is lowered in response to the pendulum movement.

8. The omnidirectional chassis of claim 1, wherein the first swivel axis, the second swivel axis, a first wheel axis and a second wheel axis are substantially parallel to one another.

9. The omnidirectional chassis of claim 1, wherein the first connecting unit, the first swivel unit and the first tandem unit each have a flat surface;

the first swivel axis is perpendicular to the flat surface of the first connecting unit and the flat surface of the first swivel unit; and the second swivel axis is perpendicular to the flat surface of the first swivel unit and the flat surface of the first tandem unit.

10. The omnidirectional chassis of claim 1, further comprising:

a second pair of omnidirectional wheels; and a second wheel suspension for the second pair of omnidirectional wheels, the second wheel suspension including a second connecting unit to connect the second wheel suspension to the rack, a second swivel unit connected to the second connecting unit via a third swivel bearing, the second swivel unit being swivel-mounted about a third swivel axis, and a second tandem unit connected to the second swivel unit via a fourth swivel bearing, the second tandem unit being swivel-mounted about a fourth swivel axis, and the fourth swivel axis being substantially parallel to the third swivel axis, wherein the second pair of omnidirectional wheels is coupled to the second tandem unit such that one omnidirectional wheel among the second pair of omnidirectional wheels is raised in response to a second swivel movement of the second tandem unit, and another omnidirectional wheel among the second pair of omnidirectional wheels is lowered in response to the second swivel movement.

11. The omnidirectional chassis of claim 10, further comprising:

a pendulum rod connected to the first swivel unit via a first self-aligning bearing, and the second swivel unit via a second self-aligning bearing.

12. The omnidirectional chassis of claim 11, further comprising:

a connecting element to connect the pendulum rod to the rack, the pendulum rod connected to the connecting element via a third self-aligning bearing, wherein the first swivel unit and the second swivel unit are coupled to the pendulum rod such that one of the first swivel unit or the second swivel unit is raised in response to a pendulum movement of the pendulum rod relative to the connecting element, and another one of the first swivel unit or the second swivel unit is lowered in response to the pendulum movement.

13. The omnidirectional chassis of claim 10, wherein at least one of
at least one omnidirectional wheel among the first pair of omnidirectional wheels or at least one omnidirectional wheel among the second pair of omnidirectional wheels includes a wheel-hub motor.

14. An arrangement, comprising:
a gantry of a computed tomography device; and
the omnidirectional chassis of claim 1 to move the arrangement relative to a support.

15. The arrangement of claim 14, wherein the omnidirectional chassis further comprises:
the rack, the omnidirectional chassis forming a mobile platform, the gantry being arranged on the mobile platform.

16. The arrangement of claim 14, wherein the gantry comprises:
a support frame that forms the rack.

17. The arrangement of claim 14, further comprising:
a patient support apparatus;
at least one marking in a region of the patient support apparatus;
a measuring system configured to record positional information relating to at least one of
a position of the omnidirectional chassis relative to the at least one marking, or
an orientation of the omnidirectional chassis relative to the at least one marking; and
a drive control unit configured to control a movement of the omnidirectional chassis based on the positional information recorded.

18. The arrangement of claim 17, further comprising:
an image reconstruction unit configured to perform a correction of an image reconstruction based on the positional information recorded.

19. A method for correcting a movement of a gantry of the computed tomography device of the arrangement of claim 14, the method comprising:
moving the gantry of the computed tomography device via an omnidirectional chassis of the arrangement along a region of an examination object to be depicted, the gantry including an X-ray source and an X-ray detector;
recording projection data from the region of the examination object via the X-ray source and the X-ray detector; during the moving of the gantry;
recording positional information relating to at least one of a position of the gantry or an orientation of the gantry during the recording of the projection data;
determining motion correction data based on the positional information recorded during the recording; and
correcting a movement of the gantry by changing at least one of a direction of a movement of the omnidirectional chassis or a speed of the movement of the omnidirectional chassis based on the motion correction data.

20. The arrangement of claim 14, wherein the gantry has a rectangular layout.

21. An arrangement, comprising:
a gantry of a computed tomography device having a substantially rectangular layout; and
the omnidirectional chassis of claim 1 to move the arrangement relative to a support, the omnidirectional chassis including four pairs of omnidirectional wheels, and each respective pair of omnidirectional wheels among the four pairs of omnidirectional wheels being on a corresponding corner among four corners of the substantially rectangular layout of the gantry.

22. The arrangement of claim 21, further comprising:
a patient support apparatus;
at least one marking in a region of the patient support apparatus;
a measuring system configured to record positional information relating to at least one of
a position of the omnidirectional chassis relative to the at least one marking, or
an orientation of the omnidirectional chassis relative to the at least one marking; and
a drive control unit, embodied to control a movement of the omnidirectional chassis based on the positional information recorded.

23. The arrangement of claim 22, further comprising:
an image reconstruction unit configured to perform a correction of an image reconstruction based on the positional information recorded.

24. The omnidirectional chassis of claim 1, wherein the second swivel axis is parallel to the first swivel axis.

25. An arrangement, comprising:
a gantry of a computed tomography device having a substantially rectangular layout; and
an omnidirectional chassis to move the arrangement relative to a support, the omnidirectional chassis including four pairs of omnidirectional wheels, and each respective pair of omnidirectional wheels among the four pairs of omnidirectional wheels being on a corresponding corner among four corners of the substantially rectangular layout of the gantry,
wherein a first pair of omnidirectional wheels among the four pairs of omnidirectional wheels is coupled to a tandem unit such that
one omnidirectional wheel among the first pair of omnidirectional wheels is raised in response to a swivel movement of the tandem unit about a swivel axis, and
another omnidirectional wheel among the first pair of omnidirectional wheels is lowered in response to the swivel movement.

26. The arrangement of claim 25, further comprising:
a patient support apparatus;
at least one marking in a region of the patient support apparatus;
a measuring system configured to record positional information relating to at least one of
a position of the omnidirectional chassis relative to the at least one marking, or
an orientation of the omnidirectional chassis relative to the at least one marking; and
a drive control unit configured to control a movement of the omnidirectional chassis based on the positional information recorded.

27. The arrangement of claim 26, further comprising:
an image reconstruction unit configured to perform a correction of an image reconstruction based on the positional information recorded.

* * * * *